United States Patent [19]

Lopez-Berestein et al.

[11] Patent Number: 4,981,690
[45] Date of Patent: Jan. 1, 1991

[54] LIPOSOME-INCORPORATED MEPARTRICIN

[75] Inventors: Gabriel Lopez-Berestein; Reeta Mehta; Roy L. Hopfer, all of Houston, Tex.; Rudolph L. Juliano, Chapel Hill, N.C.

[73] Assignee: Board of Regents, The University of Texas System, Austin, Tex.

[21] Appl. No.: 114,280

[22] Filed: Oct. 27, 1987

[51] Int. Cl.$^5$ ............................................. A61K 9/127
[52] U.S. Cl. .................................. 424/422; 424/426; 424/450; 428/402.2
[58] Field of Search ................... 424/450, 422, 426; 514/31; 428/402.2, 402.21

[56] References Cited

U.S. PATENT DOCUMENTS

| | | | |
|---|---|---|---|
| 3,773,925 | 11/1973 | Bruzzese et al. | 424/122 |
| 3,780,173 | 12/1973 | Bruzzese et al. | 424/122 |
| 4,016,100 | 4/1977 | Suzuki et al. | 424/450 |
| 4,145,410 | 3/1979 | Sears | 424/450 |
| 4,186,183 | 1/1980 | Steck et al. | 424/450 |
| 4,235,871 | 11/1980 | Papahadjopoulos | 424/450 |
| 4,241,046 | 12/1980 | Papahadjopoulos | 424/450 X |
| 4,330,534 | 5/1982 | Sakurai et al. | 514/26 |
| 4,522,803 | 6/1985 | Lenk et al. | 424/450 X |
| 4,663,167 | 5/1987 | Lopez-Berestein et al. | 514/37 |
| 4,707,470 | 11/1987 | Kirsh et al. | 514/31 |
| 4,725,442 | 2/1988 | Haynes | 424/490 |
| 4,744,989 | 5/1988 | Payne et al. | 424/490 |
| 4,766,046 | 8/1988 | Abra et al. | 424/450 |
| 4,812,312 | 3/1989 | Lopez-Berestein | 424/450 X |
| 4,863,739 | 9/1989 | Perez-Soler | 424/450 |

FOREIGN PATENT DOCUMENTS

| | | | |
|---|---|---|---|
| 0229561 | 10/1986 | European Pat. Off. | 424/450 |
| 2112426 | 6/1972 | France . | |
| 2593394 | 7/1987 | France . | |
| WO85/00968 | 3/1985 | PCT Int'l Appl. | 424/450 |
| WO86/01102 | 2/1986 | PCT Int'l Appl. | 424/450 |
| WO87/01933 | 4/1987 | PCT Int'l Appl. . | |
| WO88/03831 | 4/1989 | PCT Int'l Appl. . | |
| 1575343 | 9/1980 | United Kingdom | 264/4.1 |

OTHER PUBLICATIONS

Mehta et al., "Effect of Liposome Encapsulation on Toxicity . . . ", in *Liposomes in the Therapy of Infectious Diseases and Cancer*, (1989), Alan R. Liss, Inc., pp. 263–273.
Lopez-Berestein et al., 'Treatment and Prophylaxis . . . with Liposome-Encapsulated Amphotericin B', *J. Infect. Dis, vol. 147, No. 5 (1983), pp. 939–945*.
Chem. Abst., vol. 84, No. 25, abs. #174,021e, Bruzzese et al., *Farmaco Ed. Sci*, 31(4) 291-6, (1976).
Chem. Abst., vol. 103, No. 19, abs #157, 200h, Petrov et al., *J. Antimicrob. Chemother*, 16(2), 169–77, (1985).
Merck Index, 10th Ed., Citation #6909, p. 1011, 1983.
Merck Index, 10th Ed., Citation #611, p. 85, 1983.
Szoka, et al., Ann. Rev. Biophys. BioEng. (1980) 9:467–508.
Mehta et al., "Effect of Liposome Encapsulation on Toxicity and Antifungal Activity of Polyene Antibiotics" (1988).
Graybill, et al., J. Infect. Dis., 145:748–752 (1982).
Tremblay, et al., Abst., 1983 ICAAC No. 755, p. 222 (1983).
Graybill, et al., Abst., 1928 ICAAC No. 492, p. 152 (1982).
Mehta, et al., Biochim. Biophy. Acta, 770:230–234 (1984).
Hopfer, et al., Antimicrob. Agents and Chemo., 25:387–389 (1984).
Lopez-Berestein, et al., Cancer Drug Delivery, 1:37–42 (1983).
Partricin and Mepartricin Chemical Abstracts, pp. 1011–1012 (undated).
Search Report of Dialog Search of the Scientific Literature.

Primary Examiner—Richard D. Lovering
Assistant Examiner—John M. Covert
Attorney, Agent, or Firm—Arnold, White & Durkee

[57] ABSTRACT

The present invention involves a liposomal agent for treating disseminated fungal infection in an animal. This liposomal agent comprises the polyene antifungal compound mepartricin. The mepatricin is encapsulated within a liposome. The liposome in which the mepartri-

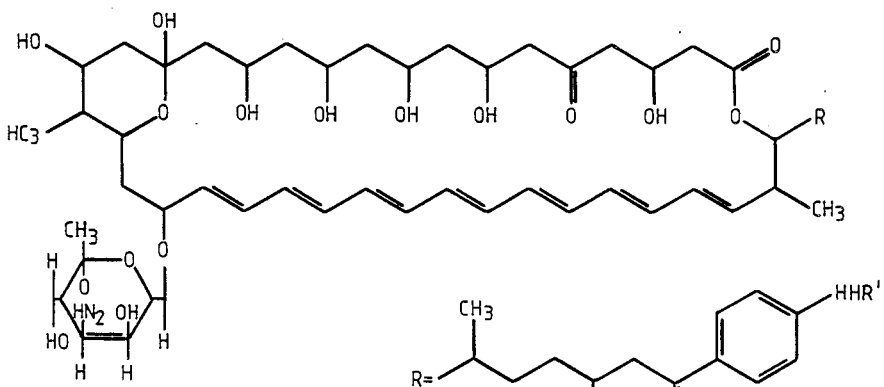

MEPARTRICIN A,
MEPARTRICIN B, $R' = CH_3$
$R' = H$ cin is incorporated is preferably a stable multilamellar vesicle. The liposome broadly comprises one or more lipids one or more of phosphomonoglyceride, phosphatidic acid and sphingolipid. The lipids are preferably one or more of phosphatidylcholine, phosphatidylserine, phosphatidylglycerol, sphingomyelin or phosphatidic acid. The lipids are most preferably one or more of dimyristoylphosphatidylchlorine, dimyristoylphosphatidylglycerol, phosphatidylcholine and phosphatidylglycerol. The liposome of the present invention may comprise a sterol most preferably cholesterol. An important aspect of the present invention involves a method for treating disseminated fungal infection in an animal. This method comprises administering to an animal subject to disseminated fungal infection a fungicidally effective amount of mepartricin encapsulated within a liposome. The liposome is composed as described above. The administering is preferably parenteral in most instances but may be oral or topical if specific colonies of fungus are thereby more directly reached. This treatment method is most useful when the animal is a human suffering from disseminated fungal infection. The method of treatment involves a fungicidally effective amount of liposome-incorporated mepartricin of between about 1 mg mepartricin/kg body weight and about 6 mg mepartricin/kg body weight.

12 Claims, 5 Drawing Sheets

MEPARTRICIN A, R' = CH₃
MEPARTRICIN B, R' = H

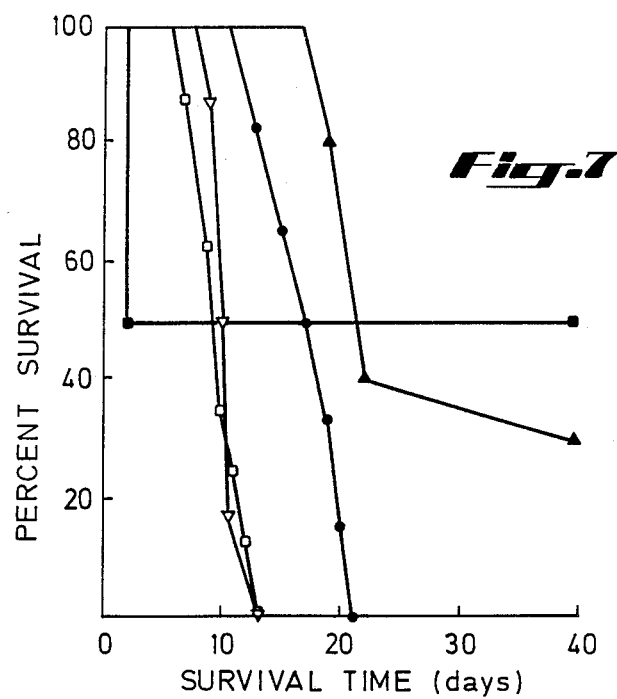
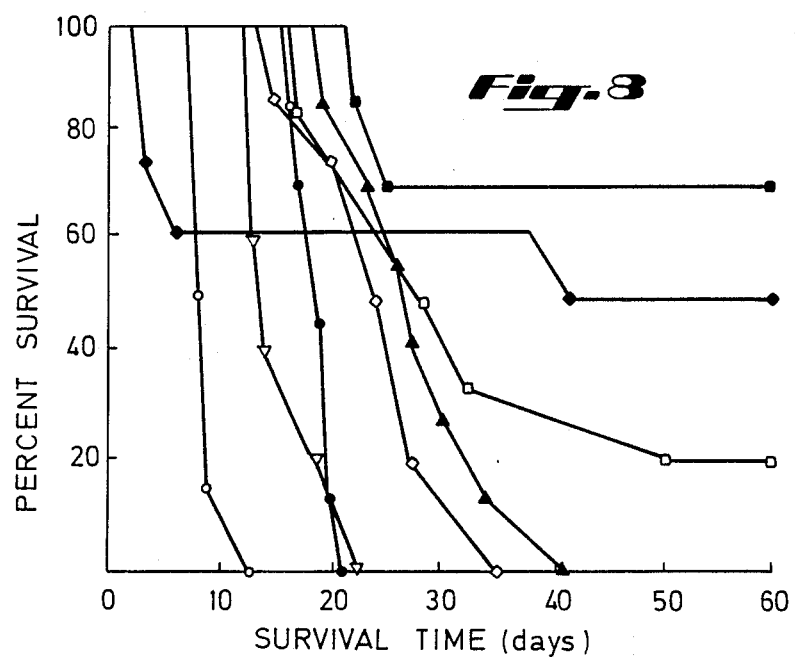

LIPOSOME-INCORPORATED MEPARTRICIN

BACKGROUND OF THE INVENTION

The development of part of the present invention was supported by contract number NIAID-NO1-AI42547 from the National Institutes of Health, Department of Health and Human Services.

The present invention relates to the treatment of systemic fungal infections by administration of liposome-incorporated mepartricin.

Clinical observations and animal experimental studies have added to the understanding of host-fungal interactions. It is becoming recognized that host defense against fungal disease is multifactorial and may vary, depending on the etiologic agent. The mechanisms of resistance are not well defined in most instances, but various innate barriers and cell-mediated immune responses seem to be of primary importance. At this time, the role of antibody in resistance is uncertain. Clearly, debilitation of innate defenses and of cell-mediated immune responses can increase an individual's susceptibility to severe fungal disease from opportunistic agents such as *Cryptococcus neoformans* and species of *Candida* and *Aspergillus*, as well as from fungal pathogens such as *Histoplasma capsulatum* and *Coccidioides immitis*. The difficulty in gaining a complete understanding of the critical host defenses has been further complicated by many studies that show fungi may affect various host immune functions adversely. Although it is too early to evaluate the clinical importance of many of these experimental findings, investigators have demonstrated that fungi impair neutrophil function, induce IgE responses, and cause suppression of cell-mediated immune responses.

Host changes likely to be associated with increased susceptibility may be accidentally induced, as in traumatic injuries (such as burns or puncture wounds); self-induced, as in chronic alcoholism; naturally occurring, as in diabetes mellitus, various congenital immune deficiencies, collagen diseases, lymphoreticular neoplastic disease, and other types of tumors; or iatrogenically induced by instrumentation (such as catheterization), surgical procedures (such as open heart surgery), or by use of cytotoxic drugs (as in an attempt to prevent graft rejection and to treat neoplastic disease), corticosteroid therapy, and long-term use of broad-spectrum antibodies.

Chemical factors that aid resistance to fungal diseases are poorly defined. Knowledge of these substances is based primarily on circumstantial evidence at the clinical level and in vitro observations at the experimental level. Hormonally associated increases in lipid and fatty acid content on the skin occurring at puberty have been correlated with increased resistance to tinea capitis caused by the dermatophyte *Microsporum audouinii*, although pubescent changes are not the sole factors in resistance. Substances in serum, cerebrospinal fluid, and saliva may limit growth of *Cryptococcus neoformans*, and basic peptides in body fluids have been shown to inhibit *Candida albicans*.

Results of clinical and experimental studies indicate that *C. albicans*, *C. neoformans*, *Aspergillus fumigatus*, and *C. immitis* activate the alternative pathway of the complement cascade. Because of the polysaccharide nature of fungal cell walls, it is expected that all medically important fungi activate complement. Such activation may be important in defense against some mycoses; a positive correlation has been demonstrated between animals deficient in late-acting complement components (C3-C9) and increased susceptibility to fungi such as *C. neoformans* and *C. albicans*. Assuming that phagocytic cells are important in resistance to fungi, complement activation may play a role by provoking an acute inflammatory response on generation of complement fragments C3a and C5a, and by coating the fungal elements with opsonic fragments C3b and C3d for ingestion by phagocytic cells.

The systemic mycoses of humans and other animals are caused by some fungi that are pathogenic and cause disease in the healthy host, and by other fungi (opportunistic pathogens) that are usually innocuous but cause disease in patients whose immune defenses are impaired. Some of these fungi may be saprophytes in nature (soil, bird droppings), whereas others are a part of the normal human flora (commensals). In no case are humans the solitary or necessary host.

An example of a soil saprophyte is *Histoplasma capsulatum*, which commonly causes infection in endemic areas; 80%-90% of adults react positively to histoplasmin in delayed cutaneous hypersensitivity tests. An example of an opportunistic pathogen is *Candida albicans*, normally present in the oral cavity, gastrointestinal tract, and probably the skin. In the patient with acute leukemia, however, *C. albicans* is commonly present in blood, causing a fulminant, usually fatal, septicemia. Other opportunistic infections are seen in patients with diabetic acidosis (mucormycosis) and Hodgkin's disease (for example, cryptococcosis and histoplasmosis). The pathogenesis of these mechanisms is obscure, but cell-mediated immunity seems to be essential for a good prognosis.

Neither active vaccines nor passive immune serum immunization has been sufficiently successful to result in commercially available preparations.

Treatment of active disease may be symptomatic (for example, pain relief), sometimes surgical (resection of irremediably damaged tissue and correction of hydrocephalus), and, most successfully, chemotherapeutic (Table 1). Among the agents commonly used are hydroxystilbamidine isethionate, amphotericin B, 5-fluorocytosine (Flucytosine), miconazole, and ketoconazole. Response to these drugs varies according to the fungus, type of disease, and course of illness. For example, response is good in most *B. dermatitidis* infections, but is poor in most diseases caused by *A. fumigatus*. Response is better for skin lesions caused by *B. dermatitidis* than for meningitis due to *C. immitis*; response is better in chronic cryptococcosis than in fulminant candidiasis. Table 1 shows a listing of some systemic mycoses and generally accepted chemotherapeutic agents.

TABLE 1

| CHEMOTHERAPEUTIC AGENTS FOR SYSTEMIC MYCOSES | | |
|---|---|---|
| Disease | First Choice | Second Choice |
| Aspergillosis | Amphotericin B | Ketoconazole |
| Blastomycosis | Amphotericin B | Hydroxystilbamidine isethionate |
| Candidiasis | Amphotericin B | Flucytosine or ketoconazole |
| Coccidioidomycosis | Amphotericin B | Ketoconazole |
| Cryptococcosis | Amphotericin B Flucytosine | Either drug alone* |
| Histoplasmosis | Amphotericin B | Ketoconazole* |
| Mucormycosis | Amphotericin B | Miconazole* |

TABLE 1-continued
CHEMOTHERAPEUTIC AGENTS FOR SYSTEMIC MYCOSES

| Disease | First Choice | Second Choice |
| --- | --- | --- |
| Paracoccidioidomycosis | Amphotericin B | Sulfonamides, Ketoconazole* |

*Depending on minimal inhibitory concentration necessary for the fungus.

Infection is the cause of death of 51% of patients with lymphoma and 75% of patients with leukemia. Although bacteria are the causative organisms of many such infections, fungi account for 13% of the fatal infections in patients with lymphoma and for more than 20% of patients with leukemia. The fungus Candida albicans causes more than 80% of these infections, and Aspergillus spp, is also a frequent cause of such infections. In addition, fungal infection is a major cause of morbidity and mortality in patients with congenital and acquired deficiencies of the immune system. Much concerted effort has been expended in search of agents useful in treating fungal infections of humans. As a result, many compounds have been isolated and shown to have antifungal activity, but problems associated with solubility, stability, absorption, and toxicity have limited the therapeutic value of most of them in human infections. The most useful antifungal antibiotics fall into one of two categories: those that affect fungal cell membranes and those that are taken up by the cell and interrupt vital cellular processes such as RNA, DNA, or protein synthesis. Table 2 lists some useful antifungal agents and their mechanism of action.

TABLE 2
SOME USEFUL ANTIFUNGAL AGENTS, THEIR CHEMICAL CLASSIFICATION, AND THEIR MECHANISMS OF ACTION

| Class | Compounds | Mechanism |
| --- | --- | --- |
| Polyene | Amphotericin B Nystatin | Interacts with sterols (ergosterol) in fungal cell membrane, -rendering cells selectively permeable to the outflow of vital constituents, e.g. potassium |
| Imidazole | Miconazole Clotrimazole Ketoconazole | Inhibits demethylation of lanosterol thus preventing formation of ergosterol, a vital component of fungal cell membrane; also has a direct cidal effect on fungal cells |
| Pyrimidine | 5-Fluorocytosine | Is taken up and deaminated by susceptible cell to form 5-fluorouracil, which in turn inhibits RNA synthesis; also thought to inhibit thymidylate synthetase and DNA synthesis |
| Grisan | Griseofulvin | Binds to tubulin and inhibits microtubule assembly |
| 3-Arylpyrrole | Pyrrolnitrin | Appears to inhibit terminal electron transport between succinate or NADH and coenzyme Q |
| Glutaramide | Cycloheximide | Inhibits protein synthesis at 80S ribosomal level preventing transfer of aminoacyl tRNA to the ribosome |

The polyene macrolide antibiotics are secondary metabolites produced by various species of Streptomyces. Several common features of these compounds are useful in classifying the more than 80 different polyenes that have been isolated. All are characterized by a macrolide ring, composed of 26–38 carbon atoms and containing a series of unsaturated carbon atoms and hydroxyl groups. These features of the molecule contribute to the polyenes' amphipathic properties (those relating to molecules containing groups with different properties, for example, hydrophilic and hydrophobic). The ring structure is closed by the formation of an internal ester or lactone bond (FIG. 1). The number of conjugated double bonds vary with each polyene, and the compounds are generally classified according to the degree of unsaturation.

Toxic effects of polyene macrolides appear to be dependent on binding to cell membrane sterols. Thus, they bind to membranes of fungus cells as well as to those of other eukaryotic cells (human, plant, and protozoa), but not to bacterial cell membranes, which do not contain membrane sterols. The interaction of polyene macrolides with mammalian and fungal membrane sterols results in transmembrane channels that allow the leakage of intracellular components leading to cell deaths.

The usefulness of an antibiotic is usually measured by the differential sensitivity of the pathogen and host. Agents such as nystatin and amphotericin B have been established as being relatively specific for fungi and therapeutically useful in humans. The relative specificity of these two polyene macrolides may be based on their greater avidity for ergosterol, the principal sterol of fungal membranes, as compared to cholesterol, the principal sterol of human cell membranes.

Amphotericin B is a heptaene macrolide with seven resonating carbon bonds. The compound was first isolated from broth filtrates of S. nodosum in 1956. Like other polyene macrolide antibiotics, amphotericin B is insoluble in water. The problem of its solubility has been partially circumvented by combining the antibiotic with sodium deoxycholate and sodium phosphate and hydrating the mixture with 5% dextrose solution. Amphotericin B, the polyene antibiotic thusfar least toxic to humans, has been used parenterally at effective doses against various fungi.

Nystatin, first isolated from S. noursei, is structurally related to amphotericin B, but is not classified as a heptaene because the conjugated portion of the ring is interrupted and thus forms a tetraene and a diene. Tolerated well both orally and topically, the drug has not been available for intravenous use because of its presumed high toxicity and aqueous insolubility. Nystatin is available as oral tablets (500,000 units) or as an ointment for topical use (100,000 units/g). It is used in the management of cutaneous and mucocutaneous candidiasis.

Partricin and mepartricin are additional antifungal polyene macrolides. Partricin is heptaene macrolide antibiotic complex produced by Streptomyces aureofaciens NRRL 3878 (see Bruzzese et al. U.S. Pat. No. 3,773,925). The structure of partricin is shown in FIG. 1. Mepartricin, a methyl ester of partricin, is also shown in FIG. 1 (see Bruzzese et al. U.S. Pat. No. 3,780,173). Mepartricin, much less toxic to animals than partricin, is therapeutically useful as an antifungal and antiprotozoan agent but again is hampered by low aqueous solubility.

It has recently been shown that the encapsulation of certain drugs in liposomes for administration to a patient can markedly alter the pharmacokinetics, tissue distribution, metabolism and therapeutic efficacy of these drugs. Liposomes may be defined as lipid vesicles which are formed spontaneously on addition of an aqueous solution to a dry lipid film. Further, the distribution and pharmacokinetics of these drugs can be modified by altering the lipid composition, size, charge and membrane fluidity of the liposomes in which they are encapsulated.

Recently, liposomes have been used as carriers of Amphotericin B for treatment of: murine leishmaniasis (New (1981) J. Antimicrob. Chemother., Vol 8, pp 371–381); histoplasmosis (Taylor et al. (1982) Ann. Rev. Respir. Dis., Vol 125, pp 610–611); cryptococosis (Graybill et al. (1982) J. Infect. Dis., Vol 145, pp 748–752); and candidiasis (Tremblay et al. (1983) Abstr. 1983 ICAAC, No. 755 (1983), p 222). Liposome-encapsulated Amphotericin B has also been used for treatment of coccidioidomycosis in the Japanese macaque (Graybill et al. (1982) Abstr. 1982 ICCAC, No. 492, p 152).

The present inventors have recently demonstrated that liposome encapsulated amphotericin B (AmpB) may be used to treat experimental murine candidiasis (Lopez-Berestein et al. (1984) J. Infect. Dis., Vol 120, pp 278–283) and in the treatment of fungal infections in patients with leukemia and lymphoma (Lopez-Berestein et al. (1985) J. Infect. Dis., Vol 151, pp 704–71- (1985).

The treatment of fungal infections remains a major problem in spite of the availability of effective antifungal drugs such as the polyenes. Most of the available polyene antibiotics have toxic side effects that limit their clinical application.

SUMMARY OF THE INVENTION

The present invention involves a composition of matter for treating disseminated fungal infection in an animal. The composition of matter comprises mepartricin and phospholipid in a liposomal form. A preferred phospholipid is phosphatidylcholine, most preferably egg phosphatidylcholine. The composition of matter of the present invention, in a preferred form, comprises a sterol and the sterol is preferably cholesterol. The most preferred composition of matter of the present invention comprises egg phosphatidylcholine and cholesterol. The phospholipids referred to above may be one or more of phosphomonoglyceride, phosphatidic acid and sphingolipid, for example but are more preferably selected from the group consisting of phosphatidylcholine, phosphatidylserine, phosphatidylglycerol, phosphatidylethanolamine, sphingomyelin and phosphatidic acid. These phospholipids are most preferably one or more of dimyristoylphosphatidylcholine, dimyristoylphosphatidylglycerol, phosphatidylcholine, phosphatidylglycerol, dipalmitoylphosphatidylcholine, distearyloylphosphatidylcholine, dioleoylphosphatidylcholine and dielaidoylphosphatidylcholine.

The composition of matter of the present invention, in a preferred embodiment, consists essentially of mepartricin, a sterol and one or more phospholipids selected from the group consisting of egg phosphatidylcholine, distearyloylphosphatidylcholine, dioleoylphosphatidylcholine and dielaidoylphosphatidylcholine. A favored composition is one which comprises the phospholipids and sterol are in a ratio of about 9:1 as well as the mepartricin and combined phospholipids—sterol having a ratio of about 1:10. The liposomal form referred to above is preferably a stable multilamellar vesicle, although other types of liposomes may be utilized.

The present invention additionally involves a method for treating disseminated fungal infection in an animal such as a human comprising administering to the animal a fungicidally effective amount of a composition of matter as described above. The administering of the composition of matter of the present invention may be oral, topical or parenteral, although parenteral is preferred. Said parenteral administration may be intravenous, intraarterial, subcutaneous, intramuscular, intralymphatic, intraperitoneal or intrapleural, although intravenous administration is preferred. A fungicidally effective amount of the composition of matter of the present invention is generally between about 1 mg mepartricin/kg body weight and about 20 mg mepartricin/kg body weight. More preferably the fungicidally effective amount is between about 2.5 mg mepartricin/kg body weight and about 6 mg mepartricin/kg body weight. For therapeutic purposes, an animal with disseminated fungal infection should be administered a pharmaceutical composition comprising mepartricin incorporated into liposomes and a pharmaceutically acceptable carrier or diluent. Such pharmaceutically accepted carriers or diluents are well-known to those skilled in the relevant arts and may be, for example, physiologically compatible, fluids such as sterile isotonic solutions.

BRIEF DESCRIPTION OF THE DRAWINGS

FIG. 7 shows the effect of various mepartricin preparations on the survival of mice infected with *C. albicans* (single-dose treatment). The animals were treated with (▽) no drug, (□) free SPA-222 at 8 mg/kg or L-SPA-160 (DOPC:PE:cholesterol, 9:3:1 liposomes) at a dose of ( ● ) 4 mg/kg, (▲) 8 mg/kg or (■) 12 mg/kg.

FIG. 8 shows the effect of various mepartricin preparations on the survival of mice infected with *C. albicans* (single and multiple dose treatment). The animals were treated with ( ● ) no drug, (▽) free SPA-222 at 8 mg/kg (single dose), (□) free SPA-222 at 8 mg/kg (five doses) or L-SPA-160 (PC:cholesterol, 9:1 liposomes) (◇) 12 mg/kg; single dose or five doses of: ( ● ) 2 mg/kg, (▲) 4 mg/kg , (■) 8 mg/kg or (◆) 12 mg/kg.

DETAILED DESCRIPTION OF THE PREFERRED EMBODIMENT

Figure 1:
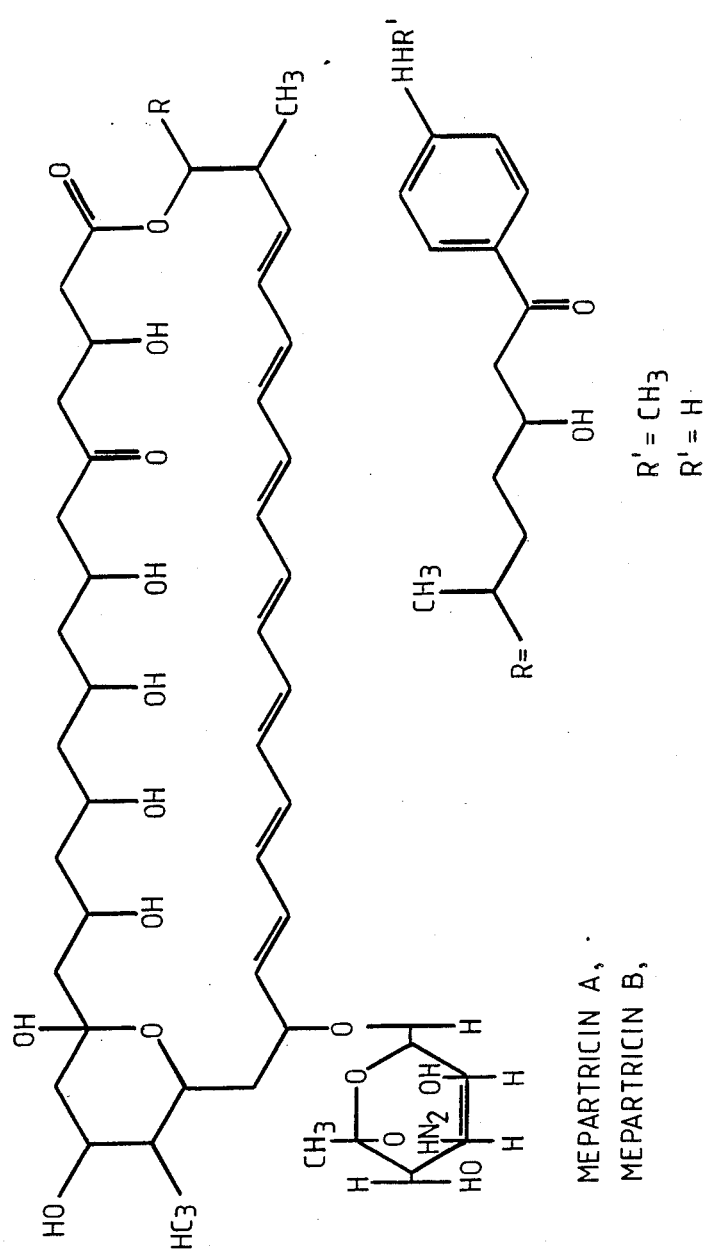
FIG. 1 schematically shows the chemical structure of mepartricin (A and B).

The use of mepartricin (SPA-160 or SPA-222) encapsulated in liposomes for the treatment of disseminated fungal infections is described herein as a new effective therapeutic method particularly useful for treatment of systemic or disseminated fungal infections. Liposome-encapsulated mepartricin has a lowered systemic toxicity and an enhanced therapeutic efficiency as compared to free mepartricin.

Although free mepartricin had antifungal activity in vitro, it was toxic and noneffective when administered intravenously. A reduced in vivo toxicity was observed with mepartricin, while the antifungal properties were maintained. These results were somewhat analogous to previous observations with liposomal-Amphotericin B, except the particular liposomal construction was of greater importance. In vivo, particular but not all liposomal mepartricin (L-SPA) preparations were found to be more than two times less toxic (maximal tolerated dose (MTD)=20 mg/kg) than free mepartricin (MTD=8 mg/kg). L-SPA at 4 mg/kg was effective in improving the survival of mice as compared with the equivalent dose of free mepartricin which showed no therapeutic effect in vivo. Further increase in survival time was achieved when higher doses of L-SPA were administered in a multiple dose regimen.

Liposomes have been extensively used to modify the therapeutic index of known active drugs. The observation with most encapsulated drugs has been that the improvement of the therapeutic index was related to reduced toxicity of free-drug after encapsulation. Free mepartricin, on the other hand, has been shown to be active orally, but its hydrophobic nature has precluded parenteral administration. The observed ineffectiveness of free mepartricin as a systemic antifungal may be due to inadequate delivery of the drug to affected sites. Liposome entrapment allowed the systemic administration of mepartricin, and its use as an active antifungal agent. The present inventors have demonstrated that liposomes enhance the delivery of amphotericin B to infected sites (Lopez-Berestein et al., Cancer Drug Delivery, Vol. 1, pp 199–205 (1986)), thus promoting the drug-drug carrier interactions with systemic fungi.

The most important aspect of the present invention involves liposomes comprising fatty substances such as phospholipids (pl), optionally cholesterol, and mepartricin, as well as the preparation and uses of these liposomes. Liposomes of the present invention comprise the mepartricin and the phospholipid in a preferred mepartricin/pl weight ratio between about 0.01/10 and about 0.7/10, a more preferred range being between about 0.02/10 and about 0.08/10. The mepartricin may be part of the phospholipid lamellae, part of the encapsulated intraliposomal fluid or both.

Preferred phospholipids of these liposomes include phosphatidylglycerol, phosphatidylcholine, sphingomyelin, phosphatidic acid or phosphatidylserine, the more preferred phospholipids being phosphatidylglycerol, phosphatidylcholine or a combination thereof. The most preferred phosphatidylcholine is one consisting essentially of egg phosphatidylcholine. When the liposomes of the present invention comprise dimyristoylphosphatidylglycerol and dimyristoylphosphatidylcholine they are preferably in a ratio between about 1–10 and 10–1, more preferably in a ratio of about 3 to 7.

The liposomes of the present invention may be multilamellar, unilamellar or have an undefined lamellar construction. A pharmaceutical composition comprising the liposomes of the present invention and a pharmaceutically acceptable carrier or diluent may be used for the therapy of disease conditions involving local or systemic fungal infections.

Such liposomes may be administered parenterally, topically or orally, parenterally being preferred for systemic or disseminated fungal infections. Parenteral dosages of liposome mepartricin (L-SPA) are generally in fungicidally effect amounts between about 1 mg mepartricin/kg body weight and about 20 mg mepartricin/kg body weight are contemplated as adequate in most conditions. The more preferable dose range is between about 2.5 mg/kg and about 6 mg/kg. The particular dosages, if an infected human is being treated may vary in each case according to the condition of the patient, the type and extent of fungal infection and directions of an attending physician.

A focal point of the present invention involves a method of treating a host animal afflicted with a fungal infection. This method comprises administering to the host an amount of a liposome of the present invention comprising a phospholipid and a fungus-inhibiting effective amount of mepartricin. The administering step is preferably parenteral and by intravenous, intraarterial, intramuscular, intralymphatic, intraperitoneal, subcutaneous, intrapleural or intrathecal injection or by topical application or oral dosage. Such administration is preferably repeated on a timed schedule, for example twice daily for a period of two weeks. The treatment may be maintained until the fungus has been eliminated and may be used in conjunction with other forms of antifungal therapy or support therapy. Such parenteral administration preferably involves L-SPA suspensions in pharmaceutically acceptable solutions such as sterile isotonic aqueous solutions. These suspensions may be obtained fully prepared or may be prepared from preformed components. As known to those skilled in the art, L-SPA may be prepared and mixed with pharmaceutically acceptable solutions to form suspensions for parenteral administration.

Topical administration of L-SPA may inVolVe pharmaceutical compositions such as suspensions, creams or ointments which may be obtained fully prepared or prepared from L-SPA precursors such as pellets. Such topical administration may be near to sites of localized fungal infection such as the epithelium or mucosa for example. Although Mepartricin has been topically used, L-SPA should more effectively inhibit fungal proliferation.

Oral administrations of L-SPA preferably involve encapsulation of L-SPA whereby the L-SPA is protected from much gastric and intestinal digestive activities before release from encapsulation.

The methods of preparation of L-SPA and chemotherapeutic treatment therewith described in the Examples contained later herein are readily adapted to the production and use of analogously described liposomes by simple substitutions of appropriate lipids or methods.

Liposomes containing mepartricin described herein may be prepared from various amphipathic substances including natural or synthetic phospholipids. The phospholipids usable to produce liposomes are numerous and not exhaustively listed herein since they are generally well known in the art. These phospholipids include but are not limited to: lecithin, phosphatidylethanolamine, lysolecithin, lysophatidylethanolamine, phosphatidylserine, phosphatidylinositol, sphingomyelin, cardiolipin, phosphatidic acid and the cerebrosides. Preferred phospholipids for the practice of aspects of the present invention include egg phosphatidylcholine, phosphatidylethanolamine, dimyristoylphosphatidylglycerol (DMPG) and dimyristoylphosphatidylcholine (DMPC), for example. A sterol such as cholesterol in proportions ranging from less than 1% to about 50% may be included with phospholipids and mepartricin to produce liposomes of the present invention. A preferable but not limiting combination of DMPG and DMPC has been found to be ratio of 3 to 7 although ratios between 1:10 and 10:1 are contemplated as satisfactory.

Either unilamellar or multilamellar or other mepartricin-containing liposomes may be used in the practice of the present invention. Multimellar liposomes are presently preferred since the mepartricin of the present invention is substantially water-insoluble. Mepartricin appears to be incorporated into the phospholipid bilayers of the liposome lamellae.

The liposome-encapsulated mepartricin of the present invention also may prove useful in the prophylaxis and/or treatment of disease caused by human T lymphotropic retrovirus, designated HTLV-III/LAV. As Gallo recently pointed out, HTLV-III/LAV may be carried in vivo by monocytes and macrophages (at p 51, Scientific American, Jan., 1987 pp 47–56). These cell types may thus serve as potentially infectious and deadly HTLV-III/LAV reservoirs. In a recently published study, Schaffner et al. (Biochem. pharmacol., V 35, pp 4110–4113 (1986)) showed data indicating that the replication of HTLV-III/LAV in the monocyte-related cell line H9 was inhibited by several antifungal polyene macrolides. These polyene macrolides included amphotericin B and amphotericin B methyl ester ascorbate. Mepartricin, although not tested, is likely to show similar results.

The phagocytes of the blood—monocytes, macrophages and polymorphonuclear leukocytes—characteristically bind and ingest foreign substances, even prior to an immune response. These phagocytes also are among the first cells to take up circulating liposomes. It appears likely that parenteral administration to an animal of liposomes comprising a polyene macrolide such as mepartricin, for example, should be useful to inhibit intracellular HTLV-III/LAV proliferation. The liposome-induced increased bioactivity of mepartricin may prove important in the control of disease caused by HTLV-III/LAV infection.

These following examples are presented to describe preferred embodiments and utilities of the present invention but are not meant to limit the present invention unless otherwise stated in the claims appended hereto.

For example, although dimyristoylphosphatidylcholine and dimyristoylphosphatidylglycerol were used to form certain liposomes, these particular lipid forms are by no means the only available usable phospholipids known to those skilled in the art. Nor do the particular formation methods for or types of liposomes used in these examples represent the only usable methods or liposome types.

EXAMPLE 1

Materials

Mepartricin (SPA-160) and mepartricin-SLS (SPA-222) were kindly supplied by Societa Prodotti Antibiotici (SPA) Milan, Italy. SPA-222 contained 2–3% of sodium lauryl sulphate (SLS) per unit weight of the complex. SPA-160 was used to make liposomes whereas SPA-222 was generally used as the free mepartricin described herein. Chromatographically pure dimyristoylphosphatidylcholine (DMPC), dimyristoylphosphatidylglycerol (DMPG) dipalmitoylphosphatidylcholine (DPPC), distearylphosphatidylcholine (DSPC), dioleoylphosphatidylcholine (DOPC), dielaidyolphosphatidylcholine (DEPC), egg yolk phosphatidylcholine (PC) and phosphatidylethanolamine (PE) were purchased from Avanti Polar Lipids (Birmingham, Ala.). Cholesterol and ergosterol were from Sigma Chemical Company (St. Louis, Mo.). Methanol for high performance liquid chromatography (HPLC), dimethyl sulfoxide (DMSO), and N, N - dimethylformamide (DMFA) were purchased from Fisher Scientific (Fair Lawn, N.J.). Human AB serum was from MA Bioproducts (Walkersville, Md.). Human RBCs were obtained from normal volunteers. All other reagents and chemicals were of analytical grade.

EXAMPLE 2

Mepartricin Characterization

The high-performance liquid chromatography of Mepartricin (HPLC) was performed with a system consisting of Water M6000A and M45 solvent delivery systems, with U6K Universal LC injector, Waters Automated gradient controller and programmer, a model 441 fixed wavelength absorbance detector, and Houston Instruments' Omniscribe recorder. Waters U-bondapak C-18 reverse-phase column (0.45 mm ×30 cm) was used for the analysis. The mobile phase consisted of methanol:0.005M EDTA (70:30) pumped at a flow rate of 2 ml/min, and the eluant was monitored for absorbance at 405 nm, 0.01 AUFS. The purity was calculated as percent peak area corresponding to Nys, divided by peak areas of total number of peaks in each chromatogram.

Figure 2:
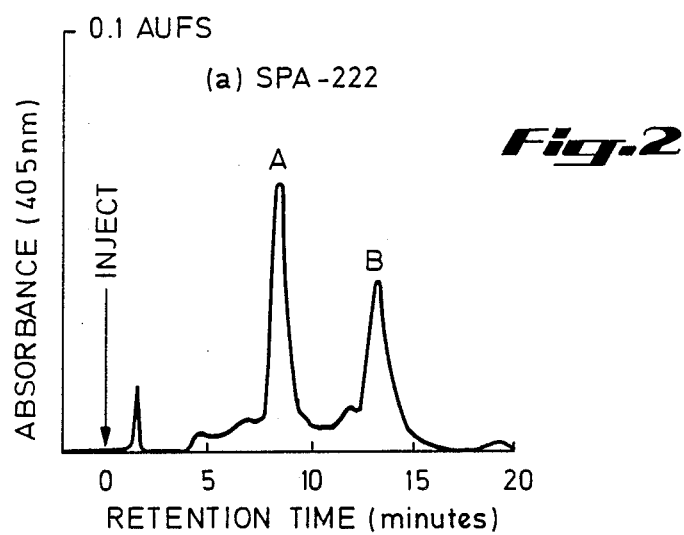
FIG. 2 shows a high-performance liquid chromatograph of mepartricin preparations used in the processes of the present invention. The peaks at 8.5 minutes and 13.5 minutes respectively correspond to mepartricin-A and mepartricin-B. The designation SPA-160 in FIG. 2 (b) indicates a mepartricin preparation as sold by SPA, Milan, Italy. The designation SPA-222 in FIG. 2 (a) indicates a mepartricin preparation with the additive sodium lauryl sulfate as sold by SPA, Milan, Italy.
Figure 2A:
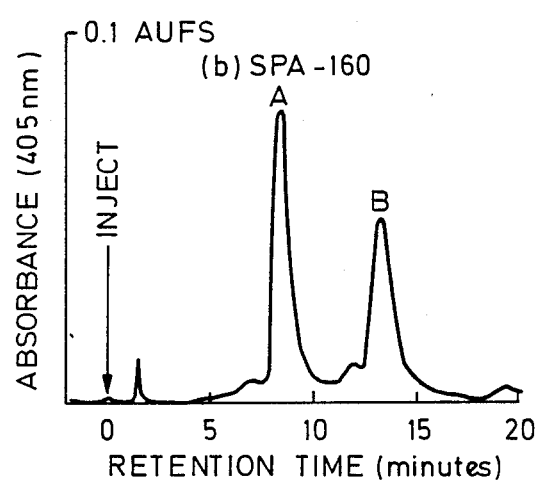

A typical chromatograph of mepartricins, SPA-222 and SPA-160 is presented in FIG. 2 *a* and *b* respectively. Two major peaks were obtained with both the analogues which correspond to Mepartricin A and B (Golik et al, (1980) J. Antibiot 33 904. The retention times of MP-A and MP-B were 8:5 min and 13:5 min. respectively. The purity of MP-A and B complex was observed to be in the range of 68 to 74%.

EXAMPLE 3

Liposome Preparation and Standardization

Multilamellar vesicles (MLV) were prepared as described previously (Lopez-Berestein et al. (1983), J. Infect. Dis., Vol. 147, 939). Mepartricin (SPA-160) was solubilized in methanol (1mg/ml) and stored at 4° C., protected from light. Phospholipids in chloroform were mixed with methanol solutions of the mepartricin and the organic solvents evaporated under partial vacuum using a rotary evaporator. The dried lipid-drug film was suspended in phosphate-buffered saline (PBS) and hand-shaken, allowing the film to form liposomes in suspension. The suspensions were then centrifuged at 20,000 rpm for 1 hr and the pellets resuspended in PBS. Liposomes comprising phospholipids and sterols at a ratio of 9:1 were similarly prepared. Amounts of mepartricin incorporated in liposomes were determined by absorbance at 380 nm. The stability of mepartricin-containing liposomes was assessed by incubating equal amounts of L-SPA-160 with PBS and human AB serum at 37° C. At indicated time intervals up to 72 hours, samples were taken out, centrifuged at 10,000 x g for 15 min and mepartricin concentration in the pellet was measured.

The encapsulation efficiency of different liposome preparations was 90–98% for a mepartricin phospholipid:sterol to ratios of up to 1:10. These liposomes were stable in PBS as well as human AB serum for up to 72 hours during which time only 0–10% of drug was released from the liposome pellets.

During the preparation of mepartricin liposomes with different lipid compositions, we observed that some of the preparations containing cholesterol or phosphatidylethanolamine resulted in aggregation of vesicles after formulation. The degree of aggregation and behavior of these aggregated vesicles differed with different lipid compositions.

EXAMPLE 4

Organism, Culture and Assay of Antifungal Activity In Vitro

*Candida albicans* strain 336 was isolated from a patient with disseminated candidiasis (Lopez-Berestein et al. (1983), J. Infect. Dis., Vol. 147, 939). Samples of this strain were grown overnight at 37° C. on Sabouraud dextrose agar plates. The resultant culture was processed for susceptibility testing (Hopfer et al. (1984) Antimicrob. Agents Chemotherap. 25 387). A twofold serial dilution method adapted to microtiter plates was used to determine the minimal inhibitory concentration (m.i.c.) of the mepartricin preparations (Shadomy et al. (1980) Manual of Clinical Microbiology, third edition, eds. Linnette et al.).

The minimal inhibitory concentration (m.i.c.) of free-mepartricin-sodium lauryl sulfate (F-SPA-222) and liposomal mepartricin (L-SPA-160) composed of various compositions is shown in Table 3. There was a general trend of L-SPA-160 showing a higher antifungal activity after encapsulation of the drug in liposomes. Empty liposomes (control without mepartricin) did not inhibit fungal growth. The m.i.c.s of L-SPA-160 were compared with those of free-SPA-222 (F-SPA-222). Empty liposomes were used as the controls.

TABLE 3

Antifungal Activity of Free Versus Liposomal-Mepartricin

| S. no. | Mepartricin preparation Type | Minimal Inhibito concentration* (ug ml) |
|---|---|---|
| 1 | Free-SPA-222 | 2.0–4.0 |
| 2 | Free-SPA-160 Liposomal-SPA-160 Lipid composition | 2.0–4.0 |

TABLE 3-continued

Antifungal Activity of Free Versus Liposomal-Mepartricin

| S. no. | Mepartricin preparation Type | Minimal Inhibito concentration* (ug ml) |
|---|---|---|
| 3 | DMPC:DMPG (7:3) | 0.2–1.0 |
| 4 | DMPC:DMPG:chol (6:3:1) | 0.4–1.0 |
| 5 | DMPC:DMPG:erg (6:3:1) | 1.0 |
| 6 | DMPC alone | 0.2 |
| 7 | DMPC:Chol (9:1) | 0.2–1.0 |
| 8 | Egg PC alone | 0.4 |
| 9 | Egg PC:chol (9:1) | 0.2–3.0 |
| 10 | DPPC alone | 0.3–3.1 |
| 11 | DPPC:chol (9:1) | 0.4 |
| 12 | DPPC:PE:chol (6.5:2.5:1) | 0.5 |
| 13 | DSPC alone | 0.4 |
| 14 | DSPC:chol (9:1) | 0.2–1.6 |
| 15 | DSPC:PE:chol (6.5:2.5:1) | 0.1 |
| 16 | DOPC alone | 0.8 |
| 17 | DOPC:chol (9:1) | 0.4–2.0 |
| 18 | DOPC:PE:chol (6:3:1) | 0.5–4.0 |
| 19 | DEPC alone | 0.5 |
| 20 | DEPC:chol (9:1) | 0.5 |
| 21 | DEPC:PE:chol (6.5:2.5:1) | 0.5 |

*The m.i.c. was determined against *Candida albicans* strain 33

EXAMPLE 5

Toxicity of Free Mepartricin and L-Mepartricin to human RBC's in vitro

Lysis of human red blood cells (HRBCs) was quantitated by measuring the release of hemoglobin in the supernatants at 550 nm, as described previously (Mehta et al., Biochim. Biophys, Acta., Vol. 770, pp. 230–234 (1984)). Various doses of L-SPA were incubated with fresh washed human RBCs at 37° C. for 45 minutes, 24 hr, 48 hr and 96 hr.

Lysis of HRBCs was quantitated by measuring the release of hemoglobin in the supernatants at 550 nm as previously described (Mehta et al., (1984) Biochem. Biophys. Acts, 770:230). Various doses of L-SPA-160 were incubated with fresh washed HRBCs at 37° C. for 45 minutes, 24, 48 and 96 hrs. Free-SPA-222, stock dissolved in water and diluted with isotonic PBS was added to the assay. F-SPA-160 as DMFA solution diluted with isotonic PBS was also used as a control and contained 3% DMFA at a final concentration of drug at 300 ug ml. Appropriate solvent controls and empty liposomes were also included in each experiment. Release of hemoglobin by hypotonic lysis of the same number of human RBCs by water was taken as 100% positive control, while cells treated with PBS were taken as negative controls.

Figure 3:
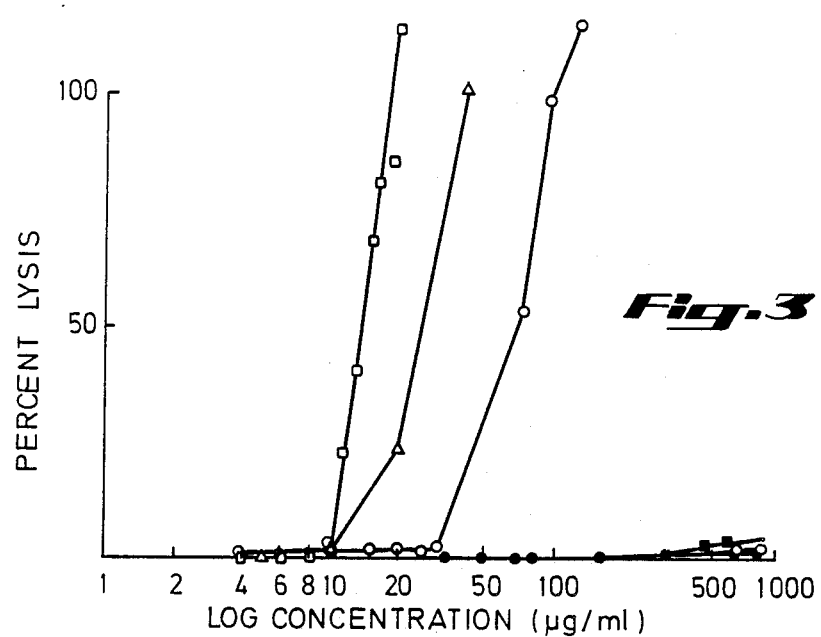
FIG. 3 shows the in vitro toxicity of sodium lauryl sulfate as well as free and liposomal mepartricin preparations to human red blood cells (RBCs). The human RBCs were incubated at 37° C. for 45 min. with ( X) free-SPA-222, (△) sodium lauryl sulfate, ( ○ ) free SPA-160, ( ● ) liposomal SPA-160 (L-SPA-160) in liposomes composed of DMPC:DMPG (7:3), (▲) L-SPA-160 in liposomes composed of DMPC:DMPG+cholesterol (9:1) or (■) L-SPA-160 in liposomes composed of DMPC:DMPG+ergosterol (9:1)
Figure 4:
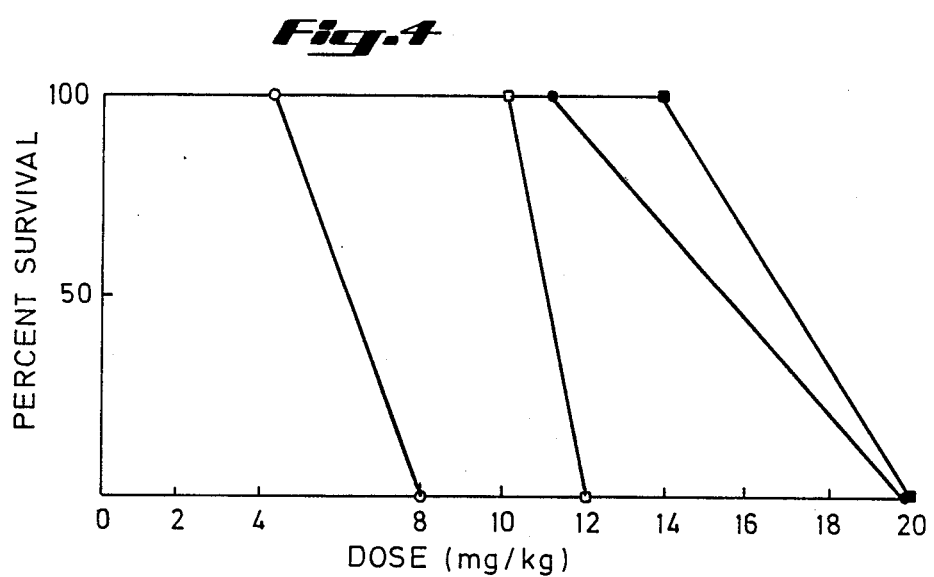
FIG. 4 shows the acute toxicity of free and liposomal mepartricin preparations in vivo. The mice were injected (iv) with ( X) free SPA-222, ( ○ ) L-SPA-160 in DMPC:DMPG (7:3) liposomes, ( ● ) L-SPA-160 in egg phosphatidylcholine (PC) cholesterol (9:1) liposomes, (▲) L-SPA-160 in DOPC:PE:cholesterol (6:3:1) liposomes or (■) L-SPA-160 in DOPC:PE:cholesterol (6.5:2.5:1) liposomes.

FIG. 3 shows the HRBC lysis produced by various doses of F-SPA-22, F-SPA-160 and L-SPA-160 composed of DMPC:DMPG (7:3) after a 45 min. incubation. F-SPA-222 showed no lysis up to lo ug ml but a linear increase in lysis was observed thereafter, reaching a maximum at a dose of 20 ug ml. With F-SPA-160, the lysis started at 30 ug ml and was maximum at a concentration of 100 ug ml. Controls with DMFA concentration up to 3% did not produce any lysis. It was interesting to note that F-SPA-222 had three to four times higher toxicity than F-SPA-160. Fifty percent of this toxicity was later found to be associated with the presence of SLS in F-SPA-222. At 20 ug ml concentration, which is present with 10 ug ml of SPA-222, SLS alone produced a 24% lysis while a 100% lysis was observed at 40 ug ml of SLS which corresponds to 20 ug ml concentration of SPA-222. On the other hand, liposomes produced no lysis up to 800 ug ml dose, regardless of the presence or absence of 30% mol% of sterols. After 24-hours incubation, liposomes composed of phospholipids only started to lyse HRBCs whereas those containing sterols produced no lysis. At 96 hours, the lysis occurred in all samples but the degree of lysis was in the following order: PL>PL;E>PL;C (where E stands for ergosterol and C is for cholesterol). These observations showed that cholesterol-containing vesicles were least toxic or more preventive of HRBC toxicity.

toxic and the recipient mice died immediately at a dose of 8 mg/kg of L-SPA-160. The liposome compositions having phosphatidylcholines with longer-chain fatty acids or 30 mole% of cholesterol were tolerated well at the 8 mg/kg dose. Dose responses with the above lipid compositions were done and the MTDs are shown in Table 4. These results show that we could buffer the toxicity of L-SPA-160 by changing the lipid composition (FIG. 4). L-SPA-160 composed of liposomes such as those containing PC+cholesterol (9:1) and DOPC-+PE+cholesterol (6:3:1) showed MTDs higher than the free drug and were used in further experiments.

TABLE 4

Toxicity of Liposomal-Mepartricin in Different Lipid Compositions

| S. no. | Lipid composition | Immediate reaction* at 8 mg/kg dose | Maximal Tolerated Dose (mg/kg) | |
|---|---|---|---|---|
| | | | Normal mice | Infected mice |
| 1 | DMPC:DMPG (7:3) | Yes | <8.0 | 4.0 |
| 2 | DMPC:DMPG:chol (6:3:1) | No | 8.0 | — |
| 3 | DMPC alone | Yes | <8.0 | — |
| 4 | DMPC:chol (9:1) | No | 12.0 | — |
| 5 | Egg PC alone | Yes | <8.0 | — |
| 6 | Egg PC:chol (9:1) | No | 20.0 | 12.0 |
| 7 | DPPC alone | No | <8.0 | — |
| 8 | DPPC:chol (9:1) | No | 8.0 | — |
| 9 | PDDC:PE:chol (6.5:2.5:1) | No | 16.0+ | — |
| 10 | DSPC alone | No | <8.0 | — |
| 11 | DSPC:chol (9:1) | No | 8.0 | — |
| 12 | DSPC:PE:chol (6.5:2.5:1) | No | 20.0 | 12.0 |
| 13 | DOPC alone | No | 8.0 | 4.0 |
| 14 | DOPC:chol (9:1) | No | 14.0 | — |
| 15 | DOPC:PE:chol (6:3:1) | No | 20.0 | 12.0 |
| 16 | DEPC alone | Yes | <8.0 | — |
| 17 | DEPC:chol (9:1) | Yes | <8.0 | — |
| 18 | DEPC:PE:chol (6.5:2.5:1) | No | 14.0 | — |

*The animals which had immediate reaction died instantly after the injection.
+Mice died after 24 hours.

Although we observed that the SPA-160 contained in liposomes composed of DMPC:DMPG (7:3) had a lessened toxicity toward red cells in vitro, these liposomes were toxic to mice at concentrations equivalent to MTD of free drug. Mepartricin-containing liposomes of various lipid compositions were tested for in vitro and in vivo toxicity of this drug. Of all the lipid compositions tested, only liposomes made of DOPC were most toxic to RBCs as compared to the free drug.

EXAMPLE 6

In vivo Toxicity of Free and Liposomal Mepartricin

Groups of 8 mice each were injected with various doses of F-SPA-222 (diluted in saline), L-SPA-160 or empty liposomes. The mice were observed for acute, subacute, and chronic toxicity and the survival time of each animal in different groups were noted (Lopez-Berestein et al., (1983) Infect. Dis., 147:939). After the indicated time periods, the surviving animals were sacrificed and blood and tissue samples were obtained. Blood biochemistry examination included blood urea nitrogen, alkaline phosphatase, and lactic dehydrogenase (LDH). The organs (liver, spleen, lungs and kidneys) were obtained and preserved in 10% formalin. Tissue slices were processed for hematoxylin-eosin and Gomori methenamine silver stains.

A number of lipid compositions tested, which were not toxic in vitro, produced considerable toxicity in mice. The maximal tolerated dose of F-SPA-222 was observed at 10 mg/kg Body wt. The toxicity pattern of L-SPA-160- of different lipid compositions is given in Table 4, Liposomes composed of phosphatidylcholine containing short chain fatty acids tended to be very

EXAMPLE 7

Therapy With Single Doses Of Free Mepartricin And L-Mepartricin For Disseminated Fungal Infection By Candida Albicans Hale-Stoner mice, six to eight weeks old (body weight 20–25 g), were purchased from The University of Texas Science Park (Bastrop, Tex.). The mice (eight per group) were injected via the tail vein with 0.2 ml of C. albicans cell suspension containing $7 \times 10^5$ colony-forming units (cfu). This concentration of cells was consistent in producing a disseminated infection after 48 hr which primarily affected liver, spleen. lungs, and kidneys.

For single dose trials, groups of 8 mice were each injected (iv) with various doses of F-SPA-222, L-SPA-160 or empty liposomes 2 days after the injection of C. albicans. The survival of the animals in each group was noted and compared with that of the untreated control group.

Figure 6:
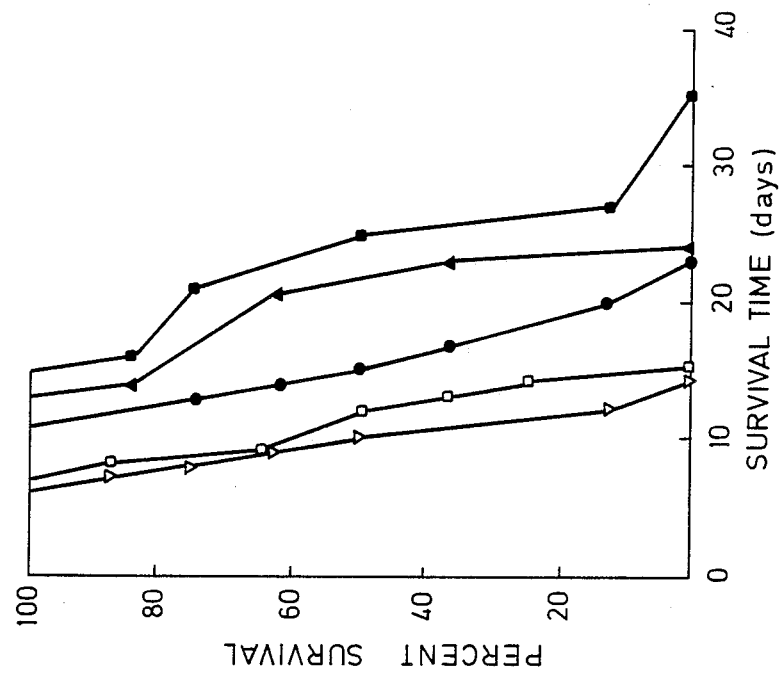
FIG. 6 shows the antifungal activity of free SpA-222 in mice. Two days after infection with C. albicans, mice were injected (iv) with (▽) no drug, or free SPA-222 at a dose of (□) 8 mg/kg, and L-SPA-160 at doses of ( ● ) 4 mg/kg, (▲)8 mg/kg, (■) 12 mg/kg.
Figure 5:
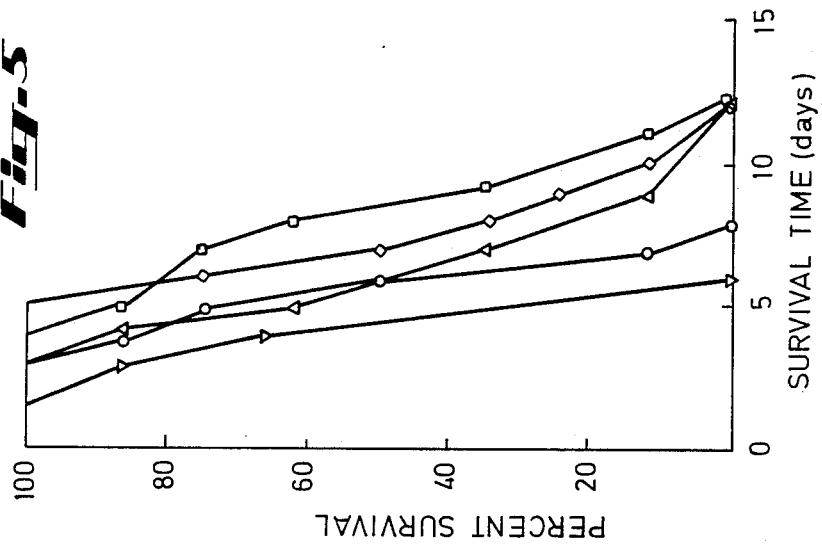
FIG. 5 shows the antifungal activity of free SPA-222 in mice. Two days after infection with C. albicans, mice were injected (iv) with (▽) no drug, or free SPA-222 at doses of: ( ○ ) 2 mg/kg, (△) 4 mg/kg, (◇) 6 mg/kg and (□) 10 mg/kg.

Mice which were treated with various doses of F-SPA-222 (range 2–10 mg/kg) showed little improvement in survival as compared to the untreated controls (FIG. 5). The survival time increased from 6 days in controls to 12 days with a dose of 10 mg/kg of F-SPA-222. The dose of 10 mg/kg was found to be the MTD. On the other hand, L-SPA-160 composed of PC+cholesterol (9:1) significantly improved the survival of mice 2-3 fold as compared to controls (4 mg:p≧008,3 mg/kg:p≧002;12 mg/kg:p≧003) (FIG. 6). Furthermore, a dose of 4 mg/kg of L-SPA-160 was significantly more effective as compared to 4 mg/kg dose of F-SPA-222 (p≥006). Similarly, 8 mg/kg dose of L-SPA-160 was significantly better than an equivalent dose of F-SPA-222 (p≥002). The median survival time (MST) was also observed to increase 2-4 fold with increasing doses of L-SPA-160 as compared to the equivalent doses of F-SPA-222. Animals survived up to 35 days with a dose of 12 mg/kg (MTD) of L-SPA in PC:cholesterol liposomes showing a significant improvement over MTD of F-SPA (p≥007).

Similar experiments were also carried out with L-SPA-160 composed of DOPC+PE+cholesterol (4;3;1). FIG. 7 shows the survival of mice treated with various doses of L-SPA-160 as compared to controls and F-SPA-222. All the animals treated with various doses of F-SPA-222 (2-8 mg/kg), empty liposomes as well as the untreated controls died within 12-15 days. The mice treated with 4 mg/kg of L-SPA-160 survived up to 21 days (≥02) while those injected with a dose of 8 mg/kg survived up to 40 days (MST=21 days;p≥03) when the experiment was terminated. A significant improvement in survival was observed when groups which were injected with L-SPA-160 were compared to those with equivalent doses of F-SPA-222 (4 mg/kg:p≥01; 8 mg/kg:p≥02). A dose of 12 mg/kg of L-SPA-160 was observed to be the $LD_{50}$ in these experiments.

Survival curves for this and other examples were calculated by the method of Kaplan and Meier (Kaplan et al. (1958) J. Amer. Stat. Assoc., 53:457) and tests for differences in survival distributions were based on a generalized Wilcoxon test (Gehan (1965) Biometrika, 52:203). Linear trend and $X^2$ test for differences in response rates among the groups and paired t-tests were used to compare the means.

EXAMPLE 8

Therapy with Multiple Doses of Free Mepartricin or L-Mepartricin for Disseminated Fungal Infections with Candida albicans Mice were infected with *C. albicans* as described in Example 7. Groups of eight mice each were injected (iv) with various doses of free mepartricin, L-SPA-160, empty liposomes or 5% DMSO two days after the injection of *C. albicans*. The survival of the animals in each group was noted and compared with that of an untreated control group.

Two days after the injection of *C. albicans* (iv), the mice were treated with different doses of F-SPA-222, L-SPA-160 or empty liposomes for 5 consecutive days. The multiple dose groups were also compared with appropriate or cumulative single doses. The animals were then observed for survival or any toxicity pertaining to the treatment with 5 daily doses. These experiments were terminated at 60 days and blood and tissue samples were collected from the surviving animals after sacrifice.

These experiments conducted with various doses of L-SPA-160 composed of PC+cholesterol only and compared with equivalent doses of F-SPA-222. Treatment of mice with five daily doses of 2 and 4 mg/kg of F-SPA-222 (p≥006 and 01 resp.) showed a survival pattern similar to a single dose of 8 mg/kg (p≥05). Five daily doses of 8 mg/kg (total dose=40 mg/kg) of F-SPA-222 improved the survival to a significant level (p≥01). An equivalent dose of L-SPA-160 (8×5=40 mg/kg) produced a marked increase in survival of mice (p≥005). However, a dose of 12 mg/kg given five times seemed to be toxic but the animals which initially tolerated the dose, survived up to the end of the experiment showing a MST of 42 days. Histopathological observations revealed that the free drug at doses up to 8 mg/kg×5 produced acute tubular necrosis in the kidneys of mice. Liposomal-drug did not produce any kidney toxicity at 8 mg/kg×5. However, a dose of 12 mg/kg×5 of L-SPA-160 showed mild acute tubular necrosis which confirms the toxicity observed in the survival pattern of these animals.

The antifungal activity of SPA-160 was maintained, after encapsulation of the drug in liposomes, irrespective of their lipid composition as reported earlier (11). The toxicity of F-SPA-222 to human RBCs was three times higher than F-SPA-160 which was later found to be due to the presence of sodium lauryl sulphate within th F-SPA-222. Hence, liposomes in this study could act as a means for avoiding the toxicity of LS present in SPA-222 and allowing the intravenous administration of SPA-160. Although less toxic than F-SPA-222, F-SPA-160 was also toxic to RBCs but the toxic effects were prevented by its encapsulation in liposomes. Cholesterol containing liposomes were observed to be most protective as observed earlier (13). This may be due to a competition between or lesser exchange of cholesterol from red cell membranes to cholesterol-containing SPA-160 liposomes. Of all the lipid compositions tested, only SPA-160 in DOPC liposomes was found to be toxic to RBCs.

The susceptibility of polyenes has been related to the overall state of membrane organization, in particular to the overall conformation of membrane components (16). Also, the binding of polyenes has been reported to increase with the increase in content of PE (5). It has also been reported the cholesterol has a stabilizing effect on egg PE and that preference of polyenes for cholesterol is lower in the presence of PE (2). Therefore, we tested addition of 30 mol% of PE to PC containing higher chain fatty acids along with 30 mol% of cholesterol to these liposomes. It was observed that we could further buffer the toxicity of SPA-160 by using the above lipid composition.

For therapeutic experiments, we selected the two lipid compositions based on the MTD values obtained in toxicity experiments. The mice treated with L-SPA-160 survived for longer time as compared to those treated with the free drug. The survival pattern was similar in both the types of liposomes except that the 12 mg/kg dose was observed to be the $LD_{50}$ in mice treated with drug in DOPC+PE+chol liposomes. PC+cholesterol liposomes for the multiple dose experiments with L-SPA-160 were used. A significant improvement in survival was observed with L-SPA-160 given in multiple doses as compared to equivalent doses of free drug or single doses of free or liposomal drug. These results suggested a requirement of continuous treatment with L-SPA-160 to obtain highly significant improvement in survival of mice with candidiasis.

In comparison with our experiment with liposomal-amphotericin-B, the present results obtained show overall that efficacy of liposomes as drug carriers may differ with similar polyenes. The same drug in different types of liposomes or liposomes composed of different lipids may behave in totally different manner. A great complexity of events occur during formulation of liposomes with lipophilic drugs and during interaction of these liposomal drugs with the target cells. The end result, however, depends on the binding of drug with the liposomal-membrane as well as on the physical state of the target cell.

Changes may be made in the elements and methods described herein or in the steps or the sequence of steps of the method described herein without departing from the concept and scope of the invention as defined in the following claims.

What is claimed is:

1. An antifungal composition comprising mepartricin, cholesterol, and phospholipid in multilamellar liposomal form, where the phospholipid and the weight ratio of phospholipid to cholesterol are selected from the group consisting of:
phosphatidylcholine and cholesterol in a ratio of about 9:1;
dioleoylphosphatidylcholine, phosphatidylethanolamine, and cholesterol in a ratio of about 6:3:1; and
dielaidoylphosphatidylcholine, phosphatidylethanolamine, and cholesterol in a ratio of about 6.5:2.5:1.

2. The composition of claim 1, where the mepartricin and the combined phospholipids and cholesterol have a weight ratio of about 1:10.

3. The composition of claim 1, where the mepartricin and phospholipids have a weight ratio between about 0.01:10 and about 0.7:10.

4. The composition of claim 1, where the mepartricin and phospholipids have a weight ratio between about 0.02:10 and about 0.08:10.

5. A method of treating disseminated fungal infection in an animal, comprising administering to an animal a fungicidally effective amount of a composition comprising mepartricin, cholesterol, and phospholipid in multilamellar liposomal form, where the phospholipid and the weight ratio of phospholipid to cholesterol are selected from the group consisting of:
phosphatidylcholine and cholesterol in a ratio of about 9:1;
dioleoylphosphatidylcholine, phosphatidylethanolamine, and cholesterol in a ratio of about 6:3:1; and
dielaidoylphosphatidylcholine, phosphatidylethanolamine, and cholesterol in a ratio of about 6.5:2.5:1.

6. The method of claim 5, where the mepartricin and the combined phospholipids and cholesterol have a weight ratio of about 1:10.

7. The method of claim 5, where the mepartricin and phospholipids have a weight ratio between about 0.01:10 and about 0.7:10.

8. The method of claim 7, where the mepartricin and phospholipids have a weight ratio between about 0.02:10 and about 0.08:10.

9. The method of claim 5, where the administration is intravenous, intraarterial, subcutaneous, intramuscular, intralymphatic, intraperitoneal, or intrapleural.

10. The method of claim 5, where the animal is a human.

11. The method of claim 5, where the fungicidally effective amount is between about 1 mg mepartricin/kg body weight and about 20 mg mepartricin/kg body weight.

12. The method of claim 5, where the fungicidally effective amount is between about 2.5 mg mepartricin/kg body weight and about 6 mg mepartricin/kg body weight.

* * * * *